United States Patent [19]

DeCarlo, Jr.

[11] Patent Number: 4,524,467
[45] Date of Patent: Jun. 25, 1985

[54] APPARATUS FOR CONSTRAINING A SOCKET BEARING IN AN ARTIFICIAL JOINT

[75] Inventor: Alfred F. DeCarlo, Jr., Stamford, Conn.

[73] Assignee: Joint Medical Products Corp., Stamford, Conn.

[21] Appl. No.: 553,518

[22] Filed: Nov. 21, 1983

[51] Int. Cl.³ .............................................. A61F 1/04
[52] U.S. Cl. ................................. 603/22; 128/92 C; 128/92 CA
[58] Field of Search .................... 3/1.91, 1.911, 1.912, 3/1.913; 128/92 C, 92 CA

[56] References Cited

U.S. PATENT DOCUMENTS

| Re. 28,895 | 7/1976 | Noiles | 3/1.912 |
| 3,903,549 | 9/1975 | Deyerle | 3/1.912 |
| 3,996,625 | 12/1976 | Noiles | 3/1.912 |
| 4,004,300 | 1/1977 | English | 3/1.913 |
| 4,040,130 | 8/1977 | Laure | 128/92 C |
| 4,150,444 | 4/1975 | Hagert | 128/92 C |
| 4,279,041 | 7/1981 | Buchholtz | 3/1.912 |

OTHER PUBLICATIONS

R. Woo, et al., "Dislocations after Total Hip Arthroplasty", *The Journal of Bone and Joint Surgery*, vol. 64-A, Dec. 1982, pp. 1295–1306.
T. Baumeister and L. Marks, *Mechanical Engineers Handbook*, McGraw-Hill, New York, pp. 8–48, 1958.

*Primary Examiner*—Richard J. Apley
*Assistant Examiner*—David J. Isabella
*Attorney, Agent, or Firm*—Maurice M. Klee

[57] ABSTRACT

A ball and socket joint for implanting in the body is provided which comprises (1) a ball; (2) a cup with a spherical cavity, said cup to be affixed to bone; (3) a projection associated with the cup and extending into the spherical cavity at the geometric pole of the cavity; and (4) a bearing member surrounding a portion of the ball and rotatable within said spherical cavity, said bearing member including a walled aperture for receiving the projection, the rotation of the bearing within the cavity being constrained by engagement of a wall of the aperture with the projection.

1 Claim, 11 Drawing Figures

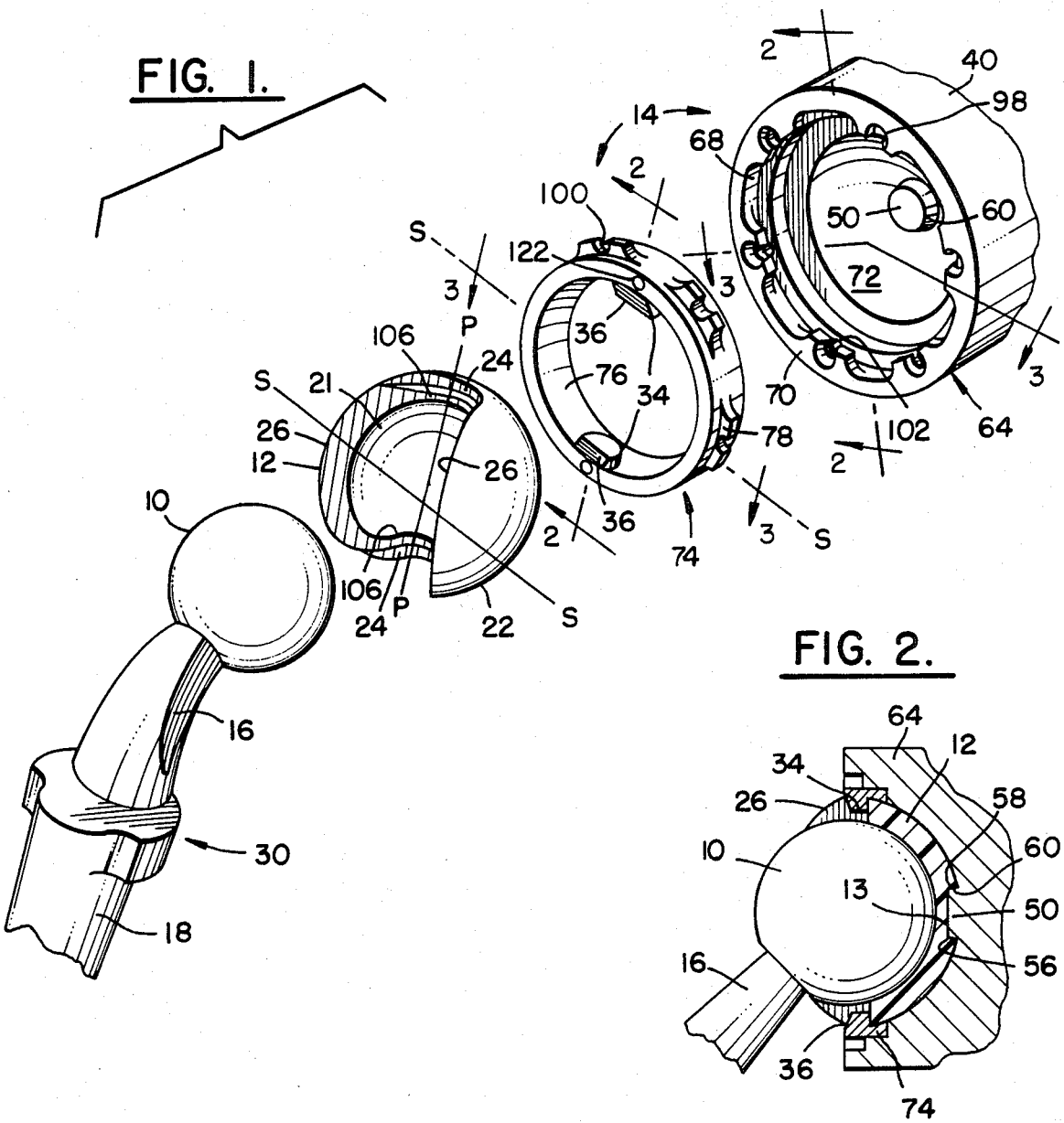
FIG. 1.
FIG. 2.
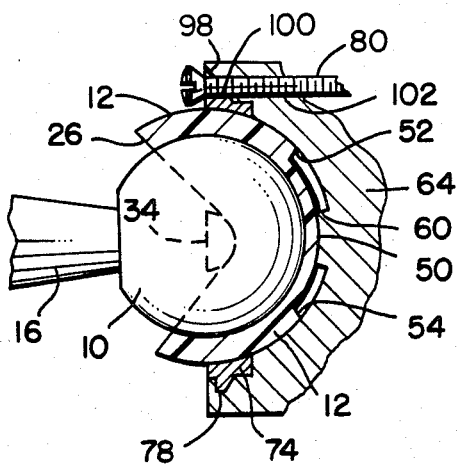
FIG. 3.
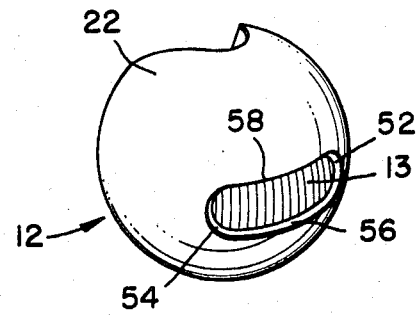
FIG. 4.

FIG. 5.
FIG. 6.
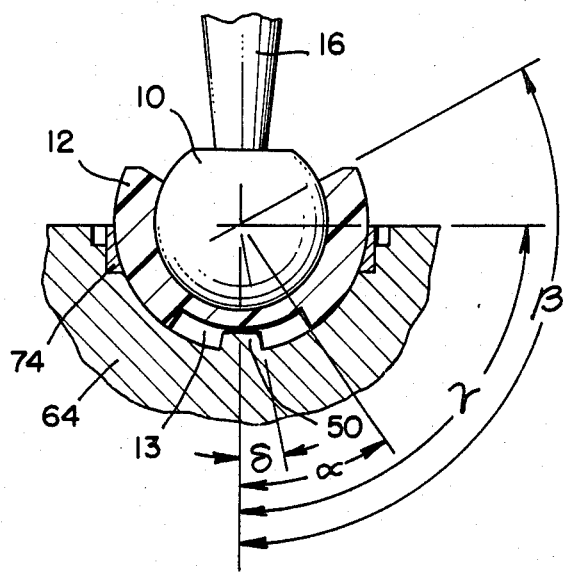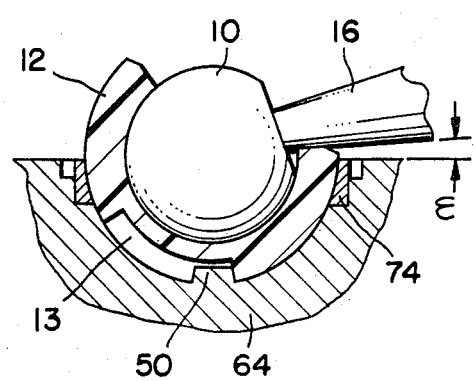

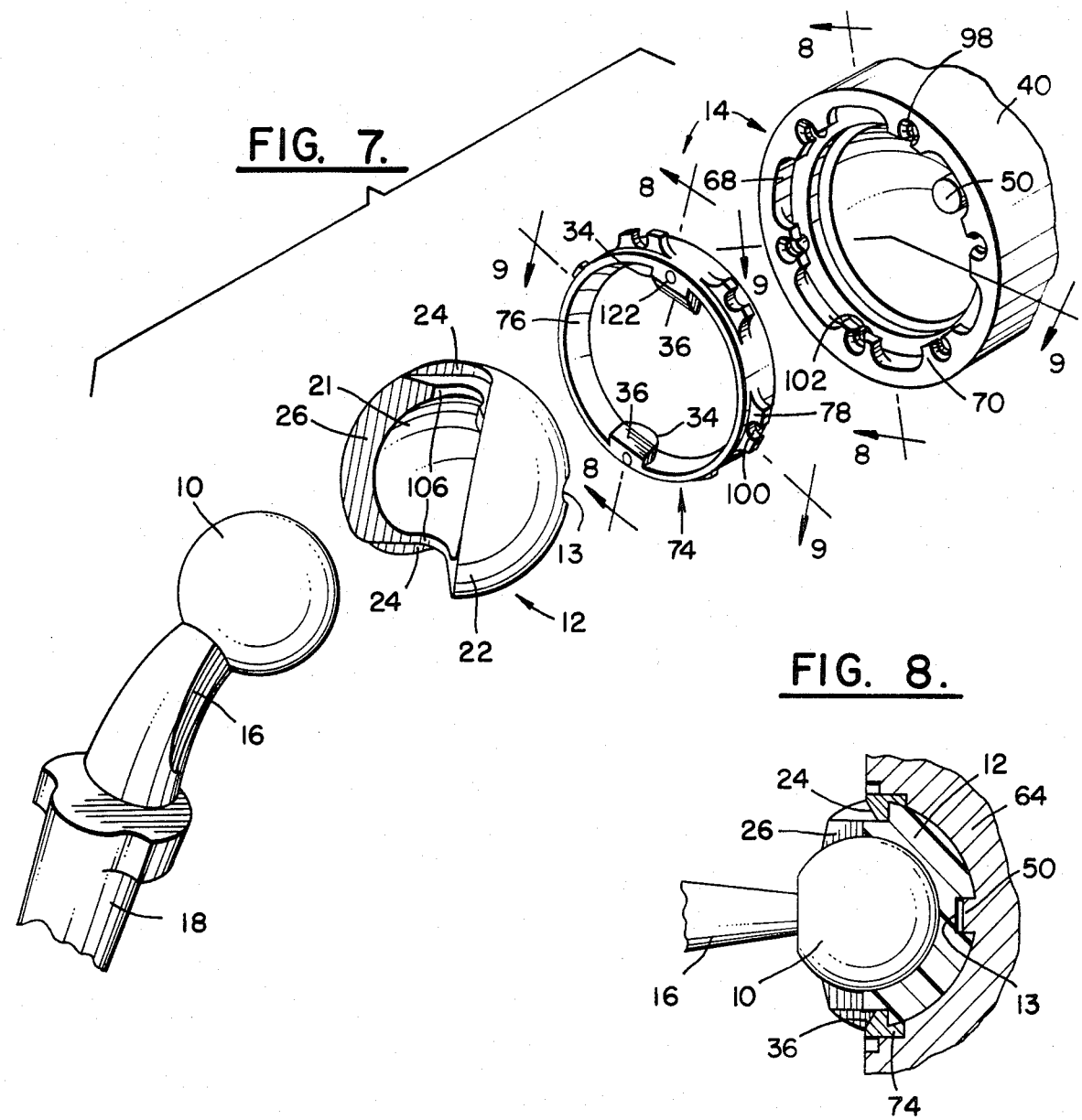

APPARATUS FOR CONSTRAINING A SOCKET BEARING IN AN ARTIFICIAL JOINT

BACKGROUND OF THE INVENTION

1. Field of the Invention

This invention relates to artificial joints and in particular to artificial joints of the ball and socket type.

2. Description of the Prior Art

As is well known in the art, artificial hip and shoulder joints conventionally employ ball and socket articulations. The socket is embedded in one body structure, for example, the pelvis for a hip reconstruction. The ball is attached to an arm composed of a neck and a stem or shaft, the stem or shaft being embedded in another bony structure, for example, the femur for a hip reconstruction.

A number of methods are known for retaining the ball in the socket. In the most common method, referred to herein as the "semi-constrained" construction, the patient's own anatomy, i.e., his muscles, tendons and ligaments, are used to retain the ball within the socket. For this construction, a hemispherical socket typically is used which allows the ball and its attached arm the maximum amount of movement without contact of the arm with the edge of the socket. The surgeon, when installing such a semi-constrained joint, aligns the ball and socket as closely as possible with the patient's natural anatomy so that the patient's movements do not tend to dislocate the ball from the joint. As a general proposition, such precise alignment is easiest the first time an artificial joint is placed in a patient. Subsequent reconstructions are much more difficult to align because of deterioration of anatomical landmarks as a result of the first operation, the healing process after the operation and changes in the anatomy caused by the presence of the artificial joint.

In order to increase the inherent stability against dislocation of such semi-constrained constructions, it has become conventional to add a cylindrical portion to the hemispherical socket to make it deeper. Although the ball is not physically constrained by the socket by this adjustment, the ball does have further to travel than if just a hemisphere had been used and thus some reduction in the propensity towards dislocation is achieved. Ball and socket joints of this type generally provide an arc or range of motion of approximately 115° when a 28 mm diameter sphere is used and the socket is made a few millimeters deeper than a hemisphere. Larger ranges of motion can be obtained by keeping the size of the arm attached to the ball constant and increasing the diameter of the ball. In this way, the angular extent of the arm relative to the ball becomes smaller. In the limit, if the ball could be made progressively larger and larger, a range of motion approaching 180° could be achieved. In practice, however, the largest sphere in common use in artificial joints, and in particular artificial hip joints, has a diameter of 32 mm and provides a range of motion of approximately 120°. It should be noted however, that such larger sphere sizes are not universally favored because frictional torque increases with diameter.

A recent study by the Mayo clinic, which appeared in the December 1982 edition of *The Journal of Bone and Joint Surgery*, reported a dislocation frequency of 3.2% for 10,500 hip joint implant procedures using the semi-constrained construction. Such dislocations essentially make the patient immobile and can necessitate a second operation. As discussed above, the critical alignment required for the semi-constrained construction is even more difficult to achieve when a second implantation is performed. Accordingly, even higher dislocation frequencies are encountered for second and subsequent implantations.

An alternative to the semi-constrained construction is the construction wherein the ball is physically constrained within the socket. In this construction, a spherically-shaped bearing surrounds the ball and serves as the socket. The bearing is attached to a fixation element which is embedded in, for example, the patient's pelvic bone. The bearing encompasses more than one-half of the ball and thus constrains the ball and its attached arm from dislocation.

The bearing is typically made from plastic, such as ultra-high molecular weight polyethylene (UHMWPE), or metal. For plastic bearings, the ball and bearing are usually assembled by forcing the bearing over the ball. The more of the ball is encompassed by the bearing, the greater the required assembly force, and the greater the constraining force to prevent postoperative dislocation of the joint. In addition, the more that the bearing encompasses the ball, the smaller the range of motion for the ball prior to contact of the bearing with the arm attached to the ball.

An example of a constrained artificial joint employing a plastic bearing is shown in Noiles, U.S. Pat. No. 3,996,625. As can be seen in FIG. 1 of this patent, a plastic bearing 17 fitted with a metal reinforcing band (un-numbered) extends beyond the diameter of the ball 24 so as to physically constrain the ball within the bearing. The bearing itself is attached to fixation element 12. The metal reinforcing band is assembled over the lip of the opening of bearing 17 after that bearing has been forced over sphere 24. The reinforcing band increases the force required to dislocate the joint. In practice, the design shown in FIG. 1 of U.S. Pat. No. 3,996,625 has been found to provide a range of motion of approximately 85° when a sphere diameter of 28 mm is used and to resist direct dislocating forces of several hundred pounds.

For constrained constructions such as that shown in U.S. Pat. No. 3,996,625, it has been found in use that a dislocating force is created when the neck of the arm attached to the ball impinges on the rim of the bearing. Because of the leverage associated with the arm and the long bone of the patient to which it is attached, e.g., the patient's femur, the dislocating force produced when the neck contacts the rim of the bearing can be considerable. For example, a force on the order of 25 pounds applied to a patient's leg can produce a dislocating force of over several hundred pounds because of the leverages involved. This type of dislocation force can be avoided by geometrically aligning the artificial joint with the patient's anatomy so that the neck does not come in contact with the rim of the bearing during normal motion of the patient's limb. That is, the leverage based dislocation forces can be avoided in the same way as dislocations are avoided in the semi-constrained construction, i.e., through precise alignment of the artificial joint with the natural anatomy of the patient. Unfortunately, as is apparent from the geometry of the situation, the more the socket bearing encompasses the ball, the greater the restraining force on the ball, but at the same time the less the range of motion prior to the neck impinging upon the edge of the bearing to create undesired leverage. In practice, artificial hips having the construction shown in U.S. Pat. No. 3,996,625 have been found to suffer dislocation due to the leverage effect in fewer than 0.5% of the implantations performed. This is significantly better than the 3.5% dislocation frequency reported in the Mayo clinic study discussed above, but an even lower dislocation frequency is obviously desirable.

A constrained construction using a metal socket bearing is shown in Noiles, U.S. Pat. No. Re. 28,895 (reissue of U.S. Pat. No. 3,848,272). This construction provides approximately a 90° range of motion when the sphere diameter is 28 mm. In a practical sense, the metal bearing can be said to be non-dislocatable. The force required to extract the metal sphere from the enclosing metal socket bearing is more than several thousand pounds. Accordingly, in use, rather than the metal ball dislocating from the metal socket bearing, any overly severe dislocating leverage will cause the fixation element to be disrupted from the bone in which it has been embedded.

As a general proposition, metal balls in metal socket bearings are used in only a minority of joint reconstructions because the medical profession is not in agreement that a metal sphere in a metal bearing is as biologically acceptable as a metal sphere in a UHMWPE plastic bearing, even though clinical use over 15 years has failed to show the metal to metal joint to be inferior to a metal to plastic joint.

A third type of artificial ball and socket joint, referred to as an endoprosthesis, eliminates the fixation element associated with the socket and simply uses a ball surrounded by a plastic socket bearing in a spherical metal head, which head is placed in the patient's natural socket but not secured to bone. For this construction, the ball can rotate within the bearing up to the rim of the bearing (the bearing is greater than a hemisphere so as to be retained on the ball), and then the bearing and its attached head rotates in the patient's socket. As with the semi-constrained construction, anatomical alignment is used to avoid dislocations, in this case between the metal head and the natural socket.

In view of the foregoing, it is apparent that in semi-constrained and endoprosthesis hip joints, reconstructive geometry of the prosthetic components is critical in ensuring the stability of the prosthesis against dislocation. Moreover, in ball and socket constructions which constrain the elements against dislocation, the range of motion inherent in the prosthesis is reduced and thus because of the possibility of leverage type dislocations, similar demands are placed on the surgeon to establish the geometry of the reconstruction within rather narrow limits.

Accordingly, an object of this invention is to provide a ball and socket joint which provides the surgeon with increased latitude in geometric positioning of the prosthetic components over those ball and socket joints presently available.

A further object of this invention is to provide a prosthetic ball and socket joint of increased inherent range of motion which is readily assembled and disassembled at the surgical site.

A further object of this invention is to provide a ball and socket bearing for an artificial joint which constrains the joint from dislocating and at the same time provides a range of motion which is greater than that available in the constructions of the constrained type described above.

An additional object of the invention is to provide a ball and socket joint having a bearing which can move within the joint through a defined range of motion.

SUMMARY OF THE INVENTION

To achieve these and other objects, the invention provides a ball and socket joint in which a ball moves within a socket bearing which is itself movable and yet constrained within a cup-like cavity of a fixation element. More particularly in accordance with the invention, a ball and socket joint for implanting in the body is provided which comprises:
  a ball;
  a cup with a spherical cavity, said cup to be affixed to bone;
  a projection associated with the cup and extending into the spherical cavity at the geometric pole of the cavity; and
  a bearing member surrounding a portion of the ball and rotatable within said spherical cavity, said bearing member including a walled aperture for receiving the projection, the rotation of the bearing within the cavity being constrained by engagement of a wall of the aperture with the projection.

The accompanying drawings, which are incorporated in and constitute part of the specification, illustrate the preferred embodiments of the invention, and together with the description, serve to explain the principles of the invention. It is to be understood, of course, that both the drawings and the description are explanatory only and are not restrictive of the invention.

BRIEF DESCRIPTION OF THE DRAWINGS

FIG. 1 is an exploded view of an artificial joint of the constrained type embodying the present invention.

FIG. 2 is a cross-sectional view along lines 2—2 in FIG. 1.

FIG. 3 is a cross-sectional view along lines 3—3 of FIG. 1.

FIG. 4 is a perspective view of the outer surface of the bearing member of the present invention.

FIGS. 5 and 6 are schematic diagrams illustrating the relationships between the angular extents of the various components of a preferred embodiment of the artificial joint of the present invention.

FIG. 7 is an exploded view of an artificial joint of the semi-constrained type embodying the present invention.

FIG. 8 is a cross-sectional view along lines 8—8 in FIG. 7.

FIG. 9 is a cross-sectional view along lines 9—9 in FIG. 7.

DESCRIPTION OF THE PREFERRED EMBODIMENTS

Figure 10:
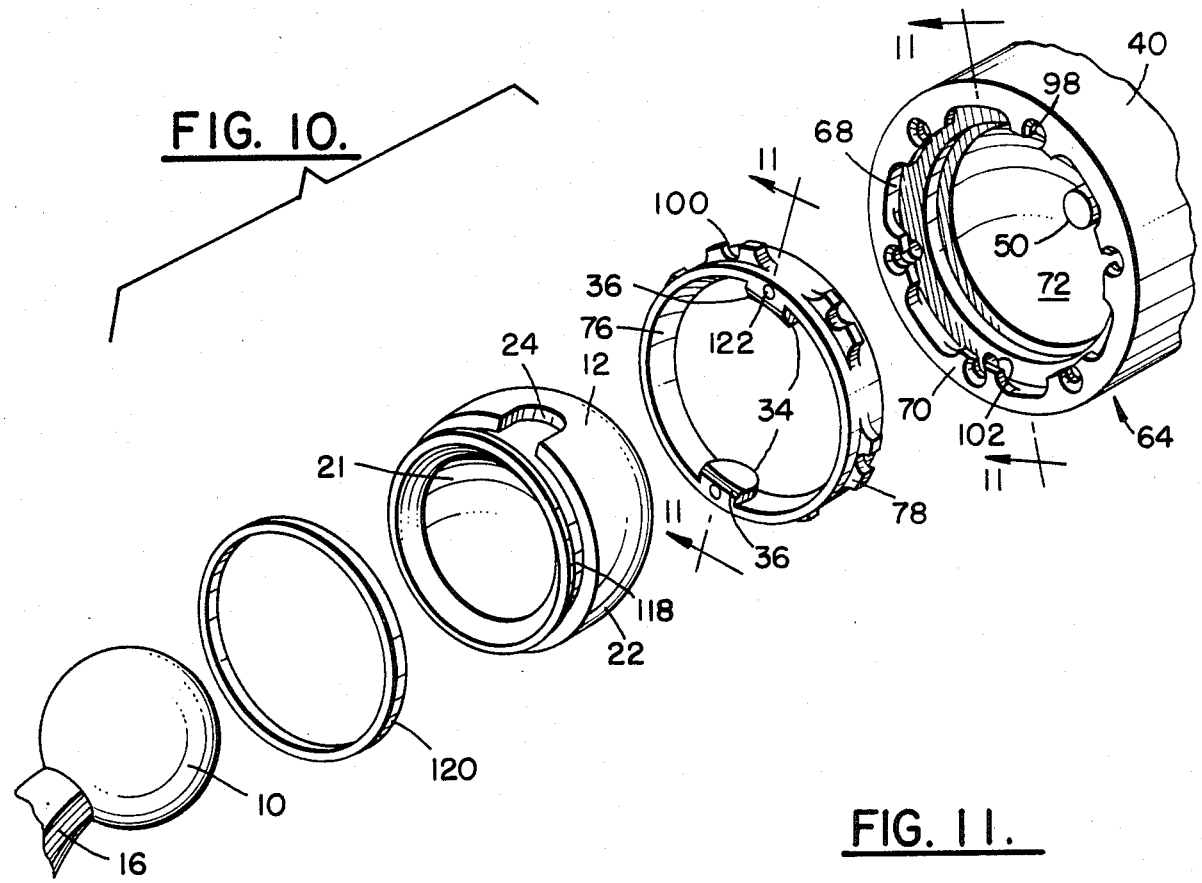
FIG. 10 is an exploded view of an artificial joint of the constrained type constructed in accordance with the present invention and including a metal reinforcing band to increase the amount of force required to dislocate the joint.

With reference now to the drawings, wherein like reference characters designate like or corresponding parts throughout the several views, there is shown in FIG. 1 a ball and socket joint constructed in accordance with the present invention and comprising ball or sphere 10, socket bearing 12 and cup 14, which consists of retaining ring portion 74 and body portion 64.

Ball 10, which is part of arm 30, is attached to stem or shaft 18 by neck 16. Stem or shaft 18 is fixed to, for example, the femur bone at the time of implant surgery.

Socket bearing 12, which preferably is made of ultrahigh molecular weight polyethylene (UHMWPE), includes inner spherical bearing surface 21, which is concentric with outer spherical bearing surface 22. Outer spherical bearing surface 22 includes walled aperture 13, whose function is described below. Cylindrical surfaces 24 of socket bearing 12 are coaxial with each other and with the center of spherical surfaces 21 and 22, and are also tangent to surfaces 26. Cylindrical surfaces 24 do not extend completely through the wall of bearing 12, but rather stop approximately halfway through to leave webs 106. So as not to interfer with the range of motion of arm 30 in the plane through lines P—P (see FIG. 1 and discussion below), the webs only extend to the height of stub pins 34 at the end of inward sloping bevels 36. The webs, although small, help restrain ball 10 within bearing 12.

As shown in FIG. 1, socket bearing 12 has an asymmetric opening which is less in one direction than it is at 90° to this one direction. Specifically, in the plane passing through the lines P—P in FIG. 1, socket bearing 12 encompasses less than one half of ball 10. In the plane passing through the lines S—S, the socket bearing has its maximum angular extent and encompasses more than half of ball 10. As discussed below in connection with FIGS. 7-11, the socket bearing can have other constructions besides that shown in FIG. 1.

When socket bearing 12 is made of a plastic material, such as, ultra-high molecular weight polyethylene, its resilience and elasticity allow it to be snapped over ball 10. The amount of interference between the equator of the ball and socket bearing 12 depends on the angular extent of the bearing's opening in the plane passing through the lines S—S in FIG. 1. The amount of interference should be such as will cause an elastic deformation of socket bearing 12 while the bearing is being assembled over the ball 10. To aid in assembly, socket bearing 12 can be heated to a non-destructive temperature (for example 70-80° C. for UHMWPE). Plastic in general, and UHMWPE in particular, has a large coefficient of thermal expansion and such thermal expansion due to heating significantly aids in assembly.

The force required to dislocate ball 10 from bearing 12 in the assembled joint is greater than the force required to place bearing 12 onto ball 10. This is so because: (1) the assembled joint operates at the body temperature of 37° C., rather than at the elevated temperature used to expand the bearing for placement onto the ball; and (2) when the joint is assembled, socket bearing 12 is captured within cup 14 by cylindrical surfaces 24 being journaled by stub half pins 34 and thus inner surface 76 of ring 74, as well as inner surface 72 of body 64, acts to at last partially prevent the bearing from deflecting outwardly, as required for the bearing to dislocate from the ball.

Socket bearing 12 is movably retained within cup 14 about an axis which is (1) parallel to the face of the cup and (2) in the direction of the greater opening in the socket bearing. More particularly, socket bearing 12 is retained within cup 14 by two stub half round pins 34 integral with portion 74 of the cup and extending part way through the wall thickness of the socket. The axes of the half round pins coincide with an axis of the spherical cup like cavity and they are also coaxial in the direction of the greater opening in the socket bearing.

When ball 1 and neck 16 of arm 30 of the prosthesis move in the direction of the lesser opening in the socket bearing, the total range of motion is the sum of the arc of motion which the neck can make within the bearing plus the arc of motion which the bearing can make within the cup. That is, for motion in the plane through line S—S in FIG. 1, neck 16 and ball 10 first move by ball 10 turning inside socket bearing 12, at the completion of which neck 16 contacts the rim of bearing 12. Thereafter, to achieve the full range of motion, ball 10 and bearing 12 rotate in unison, at the completion of which neck 16 is almost in contact with cup 14.

Normally, until neck 16 reaches the rim of socket bearing 12, socket bearing 12 will remain stationary relative to cup 14. This is so because frictional torque is the product of friction force times the distance from the center of rotation. Given similar materials, finish and geometric accuracy, so that the coefficient of friction for ball 10 and cup 14 against bearing 12 are equal, the frictional force on inner surface 21 will be the same as that on outer surface 22 when ball 10 rotates within cup 14, because the load transmitted across the two bearing surfaces is the same. Since the radius to the outer surface 22 is the greater, the frictional torque at the outer surface will be the greater and thus motion will occur along surface 21 rather than surface 22.

In general, cup 14 is approximately a hemisphere. Ball 10 can rotate until neck 16 is almost against the rim of the cup. When the diameter of the ball is approximately the 28 mm in common use, and the socket bearing wall thickness is approximately 7 mm, the inner diameter of the cup, and thus the outer diameter of the bearing, is approximately 42 mm (28 mm + 7 mm + 7 mm). Accordingly, on an overall basis, the joint functions as if it had a 42 mm ball operating in a cup of hemispherical depth. This gives the joint a range of motion in the plane through lines S—S somewhat greater than 135°, depending on the design of neck 16.

When ball 10 and neck 16 move in the direction of the greater opening in the socket bearing, their motion is limited by contact of neck 16 with webs 106 of bearing 12. That is, the neck of the prosthesis can move in the plane through lins P—P of FIG. 1 from a position of contact with lower web 106 to contact with upper web 106. To allow clearance for the movement of the neck and ball, the flat sides of the stub pins 34 are preferably beveled inwardly as shown at 36. When ball 10 has a diameter of 28 mm, the outer diameter of bearing 12 is 42 mm and beveled stub pins 34 are used, the arc or range of motion of neck 16 in the plane through lines P—P is somewhat greater than 135°, depending on the design of the neck 16.

To summarize, when motion is in the plane of stub pins 34, the total motion is by movement of ball 10 within the bearing 12. When motion is at 90° to the plane of the pins (the "90° plane"), the total motion is the sum of the motion of the ball within the bearing and the motion of the bearing within the cup. In other planes, the motion of the ball within the bearing is greater than it is in the 90° plane and the motion of the bearing within the cup is less than it is in the 90° plane.

As shown most clearly in FIG. 1, cup 14 includes two portions—body portin 64 which is affixed in the patient's bone, and retaining ring portion 74 which carries stub pins 34 and is engageable with portion 64 at a number of locations to provide a plurality of orientations for the axis through pins 34 about which socket bearing 12 rotates. This construction facilitates final assembly at the operative site, and, for hip joint replacements, allows the axis of stub pins 34 to be inclined according to the anatomical requirements of the patient as determined by the surgeon. For example, the axis can be inclined somewhat upward in the forward direction.

The exterior surface 40 of body portion 64 of cup 14 can have various contours suitable for fixation in bone whether by use of cement, or without cement by means of impaction, screwing in, or by bone ingrowth into porous metal or the like. A particularly preferred construction for the exterior surface of body portion 64 is disclosed in copending U.S. patent application Ser. No. 553,519 to Douglas G. Noiles, filed simultaneously herewith and assigned to the assignee of the present application, the pertinent portions of which are incorporated herein by reference. Cup 14 is normally made of metal which is structurally and biologically suitable for surgical implantation, such as a titanium alloy which contains 6% aluminum and 4% vanadium (see ASTM Spec. No. F136-79).

Body portion 64 is shaped to accept and hold retaining ring 74 by means of bayonet spaces 68 and lugs 70. Inner spherical surface 72 is continuous with spherical surface 76 of ring 74. Ring 74 carries stub half pin members 34 and has bayonet lugs 78.

Spherical surface 72 has associated therewith pin or projection 50. This projection is located at the geometric pole of the spherical cavity formed by spherical surfaces 72 and 76. As shown in the figures, pin 50 has sloping sides 60.

Projection 50, in combination with aperture 13 formed in outer surface 22 of bearing member 12, serves to constrain the rotation of bearing 12 so as to prevent the bearing from being rotated out of the spherical cavity once the joint is assembled and to limit the rotation of the bearing so as to keep neck 16 just out of contact with the rim of ring 74, e.g., on the order of a half a millimeter above the rim. In particular, bearing 12 can rotate only to the point where polar pin 50 and one of the end walls 52 or 54 of aperture 13 are in engagement. As discussed below, this constrained condition for bearing 12 occurs automatically as the joint is assembled without any additional assembly steps. Also, the constraining of socket bearing 12 within the joint is accomplished irrespective of the angular orientation chosen for retaining ring 74 with respect to body portion 64 of cup 14.

Aperture 13 has a long axis parallel to side walls 56 and 58 and a short axis at 90° to side walls 56 and 58. The angular extent of aperture 13 along its short axis is sufficient to accommodate polar pin 50. The angular extent of aperture 13 along its long axis determines the range of motion of socket bearing 12. As discussed above, a particularly preferred range motion for bearing 12 is one in which neck 16 is kept just out of contact with ring 74. In this case, as shown in FIGS. 5-6, the angular extent ($\alpha$) of aperture 13 along its long axis is determined by: (1) the maximum angular extent ($\beta$) of socket bearing 12; (2) the minimum angular extent ($\gamma$) of cup 14; (3) the angular extent ($\delta$) of polar pin 50; and the angular offset ($\epsilon$) of neck 16 from cup 14. In particular, the angular extent of aperture 13 is given by:

$$\alpha = \beta + \delta - \gamma - \epsilon.$$

Similar relationships can be derived for other desired ranges of motion for socket bearing 12.

The placement of pin 50 at the pole of the spherical cavity formed by surfaces 72 and 76 allows retaining ring 74 to be inserted into body portion 64 of cup 14 in any of the possible orientations provided by the mating of bayonet lugs 78 with bayonet lugs 70. That is, once socket bearing 12 is rotated about stub pins 34 until at least some portion of aperture 13 is located over the central axis of ring 74, ring 74 can be mated with body portion 64 in any of their possible relative orientations, because, for each of those orientations, aperture 13 will slip over projection 50. Since placing aperture 13 about pin 50 results in the restraining of bearing 12 in cup 14 without any further action by the surgeon, it can be seen that assembly of the joint automatically produces the desired restraining function.

A typical sequence of steps for implanting the prosthesis of the present invention in a patient are as follows. Stem 18 of arm 30 is implanted by conventional techniques in, for example, the patient's femur bone. Body portion 64 of cup 14 can also be implanted by conventional techniques, or, most preferably, by the techniques described in the above-referenced copending application to Douglas G. Noiles. Bearing 12 is assembled into ring 74 and then ball 10 is forced into bearing 12. Alternatively, bearing 12 can first be placed on ball 10 and that combination assembled into ring 74. In either case, the sub-assembly of ball 10, bearing 12 and retaining ring 74 is then inserted into body portion 64 in any of the several angular positions the bayonet lug fittings will permit, with polar pin 50 sliding into aperture 13. A fraction of a turn in either direction will engage the lugs 78 of ring 74 under lugs 70 of portion 64. Alternatively, lugs 78 can be bevelled at either their right or left hand leading edges so that insertion by rotation in only one direction is facilitated, e.g., clockwise rotation. To aid in the rotation of ring 74, the ring can include apertures 122 for engagement with a spanner wrench or the like. Note that because of the polar location of pin 50, ring 74 and its attached bearing 12 can be rotated to engage lugs 78 and 70 irrespective of where pin 50 is located along the length of aperture 13. The engagement of bayonet lugs 78 and 70 is locked by one or more screws 80 which pass through openings 98 and 100 in lugs 70 and 78, respectively, and then through holes 102 to engage the bone into which cup 64 has been implanted.

For hip joints, the possibility of a number of orientations for the axis of rotation of bearing 12 is used to place that axis in an orientation in which the greater required range of motion is aligned approximately with axis P—P. For example, the axis of rotation can be oriented upward in the forward direction to achieve this result. In this way, almost all of the highly repetitive load bearing motions of the joint will occur along or close to this axis. As discussed above, motions along or near to the axis of rotation of bearing 12 consist primarily of ball 10 moving in bearing 12, rather than bearing 12 moving in cup 14. As also discussed above, the frictional torques involved further favor movement of ball 10 in bearing 12. Accordingly, by placing the axis of rotation of bearing 12 in a favorable orientation, most repetitive motion will occur by movement of ball 10. This gives the joint low friction in that friction increases with the diameter of the moving member and ball 10 has a smaller diameter than bearing 12. Put another way, by orienting the axis of rotation of the bearing 12 in the manner described above, the joint exhibits the frictional behavior of a small ball, e.g., a 28 mm ball, for the great majority of motions of the patient's limb, while providing a range of motion corresponding to a large ball, e.g., a 42 mm ball.

Figure 11:
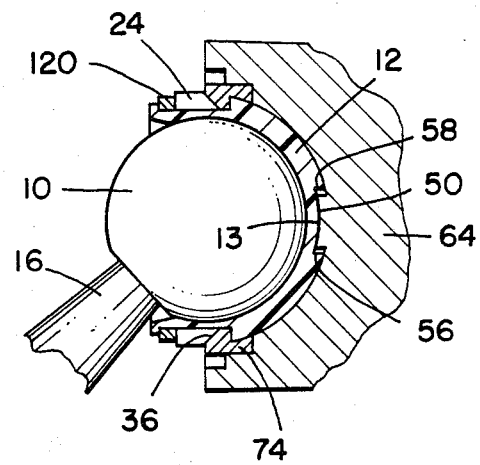
FIG. 11 is a cross-sectional view along lines 11—11 in FIG. 10.

Although the present invention has been illustrated with a socket bearing which constrains ball 10 by encompassing more than one half of ball 10 in the plane passing through lines S—S, it is to be understood that bearings which do not constrain the ball can also be used. For example, as shown in FIGS. 7-9, inner surface 21 of bearing 12 can consist of a sphere up to its equator and can have a cylindrical shape 108 thereafter so as to provide a semi-constrained type of construction. Also, to produce a constrained joint able to withstand higher dislocation forces, bearing 12 at its rim 118 can be fitted with a metal reinforcing band 120, as shown in FIGS. 10-11. For this joint, the order of assembly is first to combine bearing 12 with ring 74, then to force the bearing 12 over the ball 10 and finally to assemble band 120 to the rim of bearing 12. If the ball portion of the joint has already been implanted in the patient, this assembly order means that band 120 has to be placed over ball 10 before the bearing is mounted onto the ball.

Numerous modifications and variations of the present invention are possible in light of the above teachings. For example, ball 10, socket bearing 12, retaining ring 74 and, when used, reinforcing band 120 can be provided to the surgeon as a unit, rather than being assembled at the surgical site. Also, metal socket bearings rather than plastic bearings can be used with the invention. Further, one piece cups rather than cups consisting of a body portion and a retaining ring portion, can be used. In such a case, polar pin 50 would be constructed so that, as the joint was assembled, the pin would move out of interference with outer surface 22 of socket bearing 12 until the apertured portion of the surface was reached. For example, polar pin 50 could be spring-loaded so that it could be compressed to allow the non-apertured portion of surface 22 to pass over the pin, and then automatically spring outward into aperture 13 when the aperture was reached. It is therefore understood that within the scope of the appended claims, the invention may be practiced otherwise than as specifically described.

What is claimed is:

1. A ball and socket joint for implanting in the body which comprises:
   a ball;
   a cup with a spherical cavity, said cup including first and second elements, the first element to be affixed to bone and the second element having associated therewith two spaced apart coaxial pin members which extend into the spherical cavity and whose common axis defines an axis of rotation, said second element being moveable with respect to the first element to provide a plurality of possible orientations for said axis of rotation, said cup having a projection in the form of an axially symmetric pin extending into the spherical cavity at the geometric pole of the cavity; and
   a bearing member surrounding a portion of the ball and rotatable within said spherical cavity about said coaxial pin members, the axis of rotation of the bearing member being the axis of rotation defined by the common axis of the pin members, said bearing member including an aperture for receiving the projection, said aperture having end walls and side walls, the projection and the aperture being sized so that the projection can be received in the aperture for each of the possible orientations of the axis of rotation, the rotation of the bearing being constrained by engagement of an end wall of the aperture with the projection.

* * * * *

UNITED STATES PATENT AND TRADEMARK OFFICE
CERTIFICATE OF CORRECTION

PATENT NO. : 4,524,467
DATED : June 25, 1985
INVENTOR(S) : Alfred F. DeCarlo, Jr.

It is certified that error appears in the above-identified patent and that said Letters Patent is hereby corrected as shown below:

Column 1, line 12 "body structure" should read --bony structure--

Column 2, line 20 --which-- should be inserted before "is encompassed"

Column 5, line 56 "at last partially" should read --at least partially--

Column 6, line 1 "When ball 1" should read --When ball 10--

Column 6, line 63 "body portin" should read --body portion--

Signed and Sealed this

Third Day of February, 1987

Attest:

DONALD J. QUIGG

Attesting Officer

Commissioner of Patents and Trademarks